US007874990B2

(12) United States Patent
Nair et al.

(10) Patent No.: US 7,874,990 B2
(45) Date of Patent: Jan. 25, 2011

(54) SYSTEM AND METHOD FOR DETERMINING A TRANSFER FUNCTION

(75) Inventors: Anuja Nair, Cleveland Heights, OH (US); D. Geoffrey Vince, Avon Lake, OH (US); Jon D. Klingensmith, Shaker Heights, OH (US); Barry D. Kuban, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 2050 days.

(21) Appl. No.: 10/758,477

(22) Filed: Jan. 14, 2004

(65) Prior Publication Data

US 2005/0154315 A1 Jul. 14, 2005

(51) Int. Cl.
*A61B 8/00* (2006.01)
(52) U.S. Cl. .................................... 600/449; 600/436
(58) Field of Classification Search ................ 600/407, 600/424, 437, 443–446, 467, 469; 73/584; 128/916
See application file for complete search history.

(56) References Cited

U.S. PATENT DOCUMENTS

| 4,228,804 A | 10/1980 | Holasek |
| 4,511,984 A | 4/1985 | Sumino |

(Continued)

FOREIGN PATENT DOCUMENTS

| GB | 2 315 020 A | 1/1998 |
| WO | WO 94/23652 | 10/1994 |
| WO | WO 97/46159 | 12/1997 |
| WO | WO 01/01864 A1 | 1/2001 |

OTHER PUBLICATIONS

Adam, D., Michailovich, O., "Blind Deconvolution of Ultrasound Sequences Using Nonparametric Local Polynomial Estimates of the Pulse", IEEE Transactions on Biomedical Engineering, 2002, pp. 118-131, vol. 49, No. 2, Institute of Electrical and Electronics Engineers, New York, U.S.A.

(Continued)

*Primary Examiner*—Brian Casler
*Assistant Examiner*—Nasir Shahrestani
(74) *Attorney, Agent, or Firm*—Haynes and Boone LLP (57) ABSTRACT

A system and method is provided for using ultrasound data backscattered from vascular tissue to estimate the transfer function of a catheter (including components attached thereto—e.g., IVUS console, transducer, etc.). Specifically, in accordance with a first embodiment of the present invention, a computing device is electrically connected to a catheter and used to acquire RF backscattered data from a vascular structure (e.g., a blood vessel, etc.). The backscattered ultrasound data is then used, together with an algorithm, to estimate the transfer function. The transfer function can then be used (at least in a preferred embodiment) to calculate response data for the vascular tissue (i.e., the tissue component of the backscattered ultrasound data). In a second embodiment of the present invention, an IVUS console is electrically connected to a catheter and a computing device and is used to acquire RF backscattered data from a vascular structure. The backscattered data is then transmitted to the computing device, where it is used to estimate the catheter's transfer function and to calculate response data for the vascular tissue. The response data and histology data are then used to characterize at least a portion of the vascular tissue (e.g., identify tissue type, etc.).

11 Claims, 4 Drawing Sheets

U.S. PATENT DOCUMENTS

| | | | |
|---|---|---|---|
| 4,561,019 A | 12/1985 | Lizzi | |
| 4,575,799 A | 3/1986 | Miwa | |
| 4,858,124 A | 8/1989 | Lizzi | |
| 5,235,984 A | 8/1993 | D'Sa | |
| 5,363,850 A | 11/1994 | Soni | |
| 5,417,215 A | 5/1995 | Evans | |
| 5,445,155 A | 8/1995 | Sieben | |
| 5,485,845 A | 1/1996 | Verdonk | |
| 5,724,972 A | 3/1998 | Petrofsky | |
| 5,876,343 A | 3/1999 | Teo | |
| 5,885,218 A | 3/1999 | Teo | |
| 5,938,607 A | 8/1999 | Jago | |
| 5,957,138 A | 9/1999 | Lin | |
| 6,030,344 A | 2/2000 | Guracar et al. | |
| 6,038,468 A * | 3/2000 | Rex | 600/424 |
| 6,050,946 A | 4/2000 | Teo | |
| 6,095,976 A | 8/2000 | Nachotomy | |
| 6,106,460 A | 8/2000 | Panescu | |
| 6,106,465 A | 8/2000 | Napolitano | |
| 6,120,445 A | 9/2000 | Grunwald | |
| 6,152,878 A | 11/2000 | Nachotomy | |
| 6,200,268 B1 * | 3/2001 | Vince et al. | 600/443 |
| 6,217,517 B1 | 4/2001 | Grunwald | |
| 6,238,342 B1 | 5/2001 | Feleppa | |
| 6,254,541 B1 | 7/2001 | Teo | |
| 6,287,259 B1 | 9/2001 | Grunwald | |
| 6,306,089 B1 | 10/2001 | Coleman | |
| 6,335,980 B1 | 1/2002 | Armato | |
| 6,443,895 B1 | 4/2002 | Adam | |
| 6,454,715 B2 | 9/2002 | Teo | |
| 6,514,202 B2 | 2/2003 | Grunwald | |
| 6,544,187 B2 | 4/2003 | Seward | |
| 2001/0014774 A1 | 8/2001 | Grunwald | |
| 2003/0028118 A1 | 2/2003 | Dupree | |
| 2003/0092993 A1 | 5/2003 | Grunwald | |
| 2004/0054281 A1 | 3/2004 | Adam | |

OTHER PUBLICATIONS

Andrieu, C., Barat, E., Doucet, A., "Bayesian Deconvolution of Noisy Filtered Point Processes", IEEE Transactions on Signal Processing, 2001, pp. 134-146, vol. 49, No. 1, Institute of Electrical and Electronics Engineers, New York, U.S.A.

Kaaresen, K., "Deconvolution of Sparse Spike Trains by Iterated Window Maximization", IEEE Transactions on Signal Processing, 1997, pp. 1173-1183, vol. 45, No. 5, Institute of Electrical and Electronics Engineers, New York, U.S.A.

Kaaresen, K., "Evaluation and Applications of the Iterated Window Maximization Method for Sparse Deconvolution", IEEE Transactions on Signal Processing, 1998, pp. 609-624, vol. 46, No. 3, Institute of Electrical and Electronics Engineers, New York, U.S.A.

Kaaresen, K., Taxt, T., "Multichannel Blind Deconvolution of Seismic Signals", Geophysics, 1998, pp. 2093-2107, vol. 63, No. 6, Society of Exploration Geophysicists, Tulsa, U.S.A.

Kaaresen, K., Bølviken, E., "Blind Deconvolution of Ultrasonic Traces Accounting for Pulse Variance", IEEE Transactions on Ultrasonics, Ferroelectrics, and Frequency Control, 1999, pp. 564-573, vol. 46, No. 3, Institute of Electrical and Electronics Engineers, New York, U.S.A.

Kåresen, K., "Introduction", printed from Internet, pp. 1-9, Dec. 1999.

Michailovich, O., Adam, D., "Phase Unwrapping for 2-D Blind Deconvolution of Ultrasound Images", IEEE Transactions on Medical Imaging, 2004, pp. 7-25, vol. 23, No. 1, Institute of Electrical and Electronics Engineers, New York, U.S.A.

Moore, M., Spencer, T., Salter, D., Kearney, P., Shaw, T., Starkey, I., Fitzgerald, P., Erbel, R., Lange, A., McDicken, N., Sutherland, G., Fox, K., "Characterisation of Coronary Atherosclerotic Morphology by Spectral Analysis of Radiofrequency Signal: In Vitro Intravascular Ultrasound Study with Histological and Radiological Validation", Heart, 1998, pp. 459-467, vol. 79, No. 5, BMJ Publishing Group, London, England.

Nair, A., Kuban, B., Obuchowski, N., Vince, D., "Assessing Spectral Algorithms to Predict Atherosclerotic Plaque Composition with Normalized and Raw Intravascular Ultrasound Data", Ultrasound in Medicine and Biology, 2001, pp. 1319-1331, vol. 27, No. 10, Elsevier, New York, U.S.A.

Nair, A., Comparison of the Ability of Spectral Algorithms to Predict Atherosclerotic Plaque Composition with Radio Frequency Intravascular Ultrasound Data, Masters Thesis, cataloged on Case Western Reserve University library system Apr. 9, 2001, pp. 1-127, Case Western Reserve University, Cleveland, U.S.A.

Nair, A, Kuban, B., Tuzcu, E., Schoenhagen, P., Nissen, S., Vince, D., "Coronary Plaque Classification with Intravascular Ultrasound Radiofrequency Data Analysis", Circulation, 2002, pp. 2200-2206, vol. 106, No. 17, American Heart Association, Dallas, U.S.A.

Roan, M., Gramann, M., Erling, J., Sibul, L., "Blind Deconvolution Applied to Acoustical Systems Identification with Supporting Experimental Results", Journal of the Acoustical Society of America, 2003, pp. 1988-1996, vol. 114, No. 4, American Institute of Physics for the Acoustical Society of America, New York, U.S.A.

Spencer, T., Ramo, M., Salter, D., Sutherland, G., Fox, K., McDicken, W., "Characterisation of Atherosclerotic Plaque by Spectral Analysis of 30 MHz Intravascular Ultrasound Radio Frequency Data", IEEE Ultrasonics Symposium Proceedings, 1996, pp. 1073-1076, vol. 2, Institute of Electrical and Electronics Engineers, New York, U.S.A.

Spencer, T., Ramo, M., Salter, D., Anderson, T., Kearney, P., Sutherland, G., Fox, K., McDicken, W., "Characterisation of Atherosclerotic Plaque by Spectral Analysis of Intravascular Ultrasound: An In Vitro Methodology", Ultrasound in Medicine and Biology, 1997, pp. 191-203, vol. 23, No. 2, Elsevier, New York, U.S.A.

Taxt, T., Strand, J., "Two-Dimensional Noise-Robust Blind Deconvolution of Ultrasound Images", IEEE Transactions on Ultrasonics, Ferroelectrics, and Frequency Control, 2001, pp. 861-866, vol. 48, No. 4, Institute of Electrical and Electronics Engineers, New York, U.S.A.

Taxt, T., "Three-Dimensional Blind Deconvolution of Ultrasound Images", IEEE Transactions on Ultrasonics, Ferroelectrics, and Frequency Control, 2001, pp. 867-871, vol. 48, No. 4, Institute of Electrical and Electronics Engineers, New York, U.S.A.

Watson, R., McLean, C., Moore, M., Spencer, T., Salter, D., Anderson, T., Fox, K., McDicken, W., "Classification of Arterial Plaque by Spectral Analysis of In Vitro Radio Frequency Intravascular Ultrasound Data", Ultrasound in Medicine and Biology, 2000, pp. 73-80, vol. 26, No. 1, Elsevier, New York, U.S.A.

Nair et al., "'Blind'" Data Calibration of Intravascular Ultrasound Data for Automated Tissue Characterization, Ultrasonics Symposium, 2004 IEEE Montreal, Canada, (Aug. 23-27, 2004), vol. 2, pp. 1126-1129.

Kaaresen et al., "Blind Deconvolution of Ultrasonic Traces Accibunting for Pulse Variance," IEEE Transactlions on Ultrasonics Ferroelectrics and Frequenty, Control, IEEE, vol. 46, No. 3 (May 1, 1999), pp. 564-573.

Nair et al., "Accessing Spectral Algorithms to Predict Atherosclerotic Plaque Composition With Normalized and Raw Intravascular Data," Ultrasound in Medicine and Biology, New York, NY, vol. 27, No. 10 (Oct. 1, 2001) pp. 1319-1331.

Nair et al., "Classification of Atherosclerotic Plaque Composition by Spectral Analysis of Intravascular Ultrasound Data," 2001 IEEE Ultrasonics Symposium Proceedings, Atlanta, GA (Oct. 7-10, 2001) vol. 2, pp. 1569-1572.

Kaaresen, "Deconvolution of Sparse Spike Trains by Iterated Window Maximization," IEEE Transactions on Signal Processing, IEEE Service Center, New York, NY, vol. 45, No. 5 (May 1, 1997) pp. 1173-1183.

European Search Report for EP 04707376.2 dated Mar. 27, 2009.

* cited by examiner

SYSTEM AND METHOD FOR DETERMINING A TRANSFER FUNCTION

BACKGROUND OF THE INVENTION

1. Field of the Invention

The present invention relates to the intravascular-ultrasound (IVUS) arts, or more particularly, to a system and method of using ultrasound data backscattered from vascular tissue to estimate the transfer function of a catheter (including components attached thereto—e.g., IVUS console, transducer, etc.).

2. Description of Related Art

Ultrasound imaging of the coronary vessels of a patient can provide physicians with valuable information. For example, such an image may show the extent of a stenosis in a patient, reveal progression of disease, determine the vulnerability of the atherosclerotic plaque for causing myocardial infarction, help determine whether procedures such as angioplasty or atherectomy are indicated, or whether more invasive procedures are warranted.

In a typical ultrasound imaging system, a catheter (including an ultrasonic transducer attached thereto) is carefully maneuvered through a patient's blood vessel to a point of interest. Acoustic signals are then transmitted and echoes (or backscatter) of the acoustic signals are received. The backscattered ultrasound data ("backscattered data") can be used to identify the type or density of the tissue being scanned. When the echoes (or multiple sets thereof) are received, acoustic lines are processed, building up a sector-shaped image of the blood vessel. After the backscattered data is collected, an image of the blood vessel (i.e., an intravascular-ultrasound (IVUS) image) is reconstructed using well-known techniques. This image is then visually analyzed by a cardiologist to assess the vessel components and plaque content.

One drawback of such a system, however, is that the ultrasound data backscattered from the vascular tissue may not accurately represent the tissue. This is because the backscattered data may further include a noise component and a catheter component. For example, with respect to the latter, manufacturing tolerances can cause different catheters (or devices connected thereto—e.g., IVUS console, transducer, etc.) to operate differently (e.g., at slightly different frequencies, etc.), thus producing different results. This influence on the system is referred to herein as the "transfer function."

Traditionally, the transfer function has been determined (i) with the catheter outside the patient and (ii) through the use of a perfect reflector (e.g., plexiglass, etc.). Specifically, the catheter would be positioned near the reflector and used to transmit ultrasound data toward the reflector and to receive ultrasound data backscattered from the reflector. Because the reflector backscatters all (or substantially all) of the data transmitted, the catheter's transfer function can then be computed. This is because the backscattered data (B) is equal to the transmitted data (T) as modified by the transfer function (H) (i.e., $B=TH$). Drawbacks of such a system, however, are that the transfer function cannot be computed in real-time (e.g., while data backscattered from vascular tissue is being acquired, etc.) and requires the use of additional components (e.g., a perfect reflector, etc.). Thus, it would be advantageous to have a system and method for determining the transfer function of a catheter that overcomes at least one of these drawbacks.

SUMMARY OF THE INVENTION

The present invention provides a system and method of using ultrasound data backscattered from vascular tissue ("backscattered data") to estimate the transfer function of a catheter, which can then be used to calculate response data for the vascular tissue. Embodiments of the present invention operate in accordance with a catheter having at least one transducer, a computing device, and a transfer-function application. Specifically, in accordance with a first embodiment of the present invention, the computing device is electrically connected to the catheter and used to acquire RF backscattered data from a vascular structure (e.g., a blood vessel, etc.). This is accomplished by maneuvering the transducer portion of the catheter through the vascular structure to a point of interest and pulsing the transducer to acquire echoes, or data backscattered from vascular tissue. The transfer-function application is then adapted to use the backscattered data and an algorithm to estimate the transfer function of the catheter. The transfer function can then be used (at least in a preferred embodiment) to calculate response data for the vascular tissue (i.e., the "pure" tissue component of the backscattered data).

In one embodiment of the present invention, the algorithm is an iterative algorithm that is time-invariant over small intervals. In another embodiment of the present invention, the algorithm executes multiple underlying equations (e.g., an error-criteria equation, a least-squares-fit equation, etc,) and/or rely on certain selected or pre-specified parameters (e.g., a scale parameter, a shift parameter, a sign parameter, etc.). In another embodiment of the present invention, the algorithm may further be used to estimate response data for the vascular tissue. Thus, for example, execution of the algorithm may produce estimated values for both the transfer function and the response data.

The transfer function's influence on the backscattered ultrasound data can be represented with the frequency domain equation $Z(\omega)=X(\omega)H(\omega)+E(\omega)$, where Z is the backscattered data, X is the response data for vascular tissue, H is the transfer function, and E is the noise (or error) component of the backscattered data. In one embodiment of the present invention, the transfer function (H) and the backscattered data (Z) are used to calculate the response data (X) (e.g., $X=Z/H$). In another embodiment of the present invention, the transfer function (H), the backscattered data (Z), and the estimated response data ($X_{est}$) are used to calculate the response data (X). For example, the transfer function (H) and the backscattered data (Z) could be used to calculate response data ($X_{cal}$) (e.g., $X_{ca}=Z/H$), and the calculated response data ($X_{cal}$) and the estimated response data ($X_{est}$) could be used to calculate the response data (X) (e.g., final response data where X is a function of $X_{cal}$ and $X_{est}$). In another embodiment of the present invention, the estimated response data ($X_{est}$), alone (i.e., without the calculated response data ($X_{cal}$)), is used to calculate the response data (X) (e.g., $X_{est}=X$, etc.) In another embodiment of the present invention, the transfer-function application is further adapted to filter out the noise component (E) of the backscattered data (Z).

In a second embodiment of the present invention, an IVUS console is electrically connected to a catheter having at least one transducer and a computing device, wherein the computing device includes a transfer-function application, a characterization application, and a database. Specifically, the IVUS console is used to acquire RF backscattered data from a vascular structure (e.g., via the catheter). The backscattered data is then transmitted to the computing device, where it is used by the transfer-function application to estimate the transfer function (H) and to calculate the response data (X) (as previously discussed). Parameters of the response data (X) are then compared (i.e., by the characterization application) with histology data stored in the database in an effort to characterize the vascular tissue (e.g., identify tissue type, etc.).

Specifically, prior to the calculation of response data (X), parameters are stored in the database and linked to characterization data (tissue types, etc.). After the response data (X) is calculated, the characterization application is used to identify at least one parameter associated (either directly or indirectly) with the response data (X). The identified parameters are then compared to the parameters stored in the database (i.e., histology data). If a match (either exactly or substantially) is found, the related region (e.g., vascular tissue or a portion thereof) is correlated to the tissue type (or characterization) stored in the database (e.g., as linked to the matching parameter(s)). In another embodiment of the present invention, the characterization application is further adapted to display a reconstructed image of at least a portion of the interrogated vascular structure on a display (e.g., using gray-scales, colors, etc.).

A more complete understanding of the system and method of using ultrasound data backscattered from vascular tissue to estimate the transfer function of a catheter will be afforded to those skilled in the art, as well as a realization of additional advantages and objects thereof, by a consideration of the following detailed description of preferred embodiments. Reference will be made to the appended sheets of drawings which will first be described briefly.

DETAILED DESCRIPTION OF THE PREFERRED EMBODIMENT

Preferred embodiments of the present invention operate in accordance with a catheter having at least one transducer, a computing device, and a transfer-function application operating thereon. In the detailed description that follows, like element numerals are used to describe like elements illustrated in one or more figures.

Figure 1:
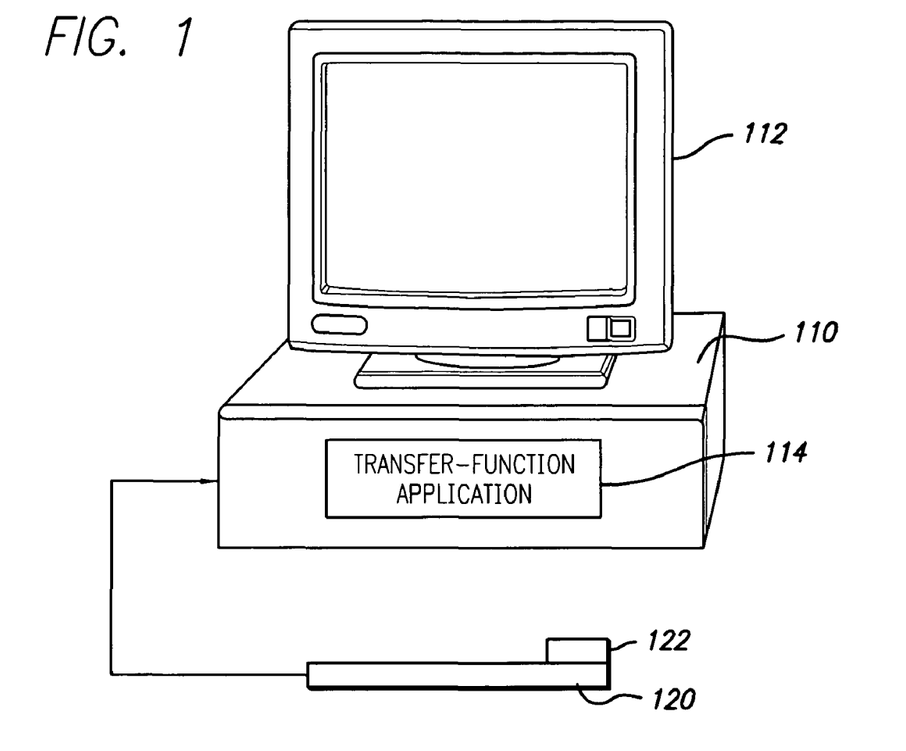
FIG. 1 illustrates an intravascular-ultrasound (IVUS) data-acquisition system in accordance with one embodiment of the present invention, including a computing device and a catheter having a transducer.
Figure 2A:
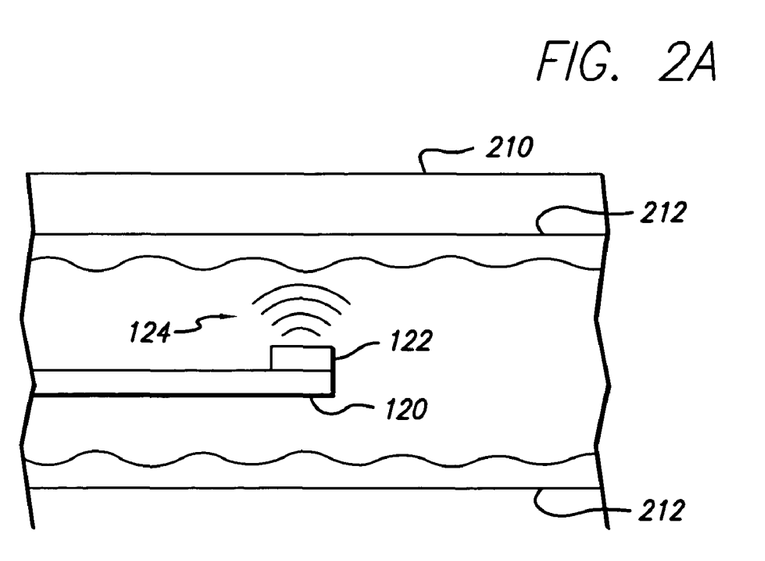
FIG. 2A illustrates a catheter and a transducer operating inside a vascular structure.

FIG. 1 illustrates an intravascular-ultrasound (IVUS) data-acquisition system operating in accordance with a first embodiment of the present invention. In this embodiment, a computing device 110 is electrically connected to a catheter 120 and used to acquire RF backscattered data from a vascular structure (e.g., a blood vessel, etc.). Specifically, as shown in FIG. 2A, the transducer 122 is attached to the end of the catheter 120 and maneuvered through a vascular structure 212 of a patient 210 to a point of interest. The transducer 122 is then pulsed (see e.g., 124) to acquire echoes or backscattered data reflected from the tissue of the vascular structure (see FIG. 2C). Because different types and densities of tissue absorb and reflect ultrasound data differently, the reflected data (i.e., backscattered data) can be used to image the vascular object. In other words, the backscattered data can be used (e.g., by the computing device 110) to create an image of the vascular tissue (e.g., an IVUS image, a tissue-characterization image, etc.). Exemplary images can be seen in FIGS. 4 and 5 of U.S. Pat. No. 6,200,268, issued on Mar. 13, 2001, and in FIGS. 2 and 5 of patent application Ser. No. 10/647, 971, filed on Aug. 25, 2003 and claiming priority to Provisional Application Nos. 60/406,254, 60/406,148, and 60/406, 183; collectively filed on Aug. 26, 2002; all of which are incorporated herein, in their entireties, by reference.

In another embodiment of the present invention, the computing device 110 further includes a display 112 (e.g., to display the aforementioned image). It should be appreciated that the computing devices depicted herein (i.e., 110 and 330) include, but are not limited to, personal computers, mainframe computers, PDAs, and all other computing devices, including medical (e.g., ultrasound devices, thermographic devices, optical devices, MRI devices, etc.) and non-medical devices, generally known to those skilled in the art. It should also be appreciated that the term "catheter" is used herein in its broad sense, encompassing both the catheter and components attached thereto (e.g., IVUS console, transducer(s), etc.). Thus, for example, while the specification may state that the catheter transmits an ultrasound signal, those skilled in the art will realize that it is actually the transducer portion of the catheter that actually transmits the ultrasound signal. Similarly, while the specification refers to estimating the catheter's transfer function, those skilled in the art will realize that such an estimation further includes the transfer function of components attached thereto (e.g., transducer, IVUS console, etc.). It should further be appreciated that the catheters depicted herein (i.e., 120 and 320) are not limited to any particular type, and include all catheters generally known to those skilled in the art. Thus, for example, a catheter having a single transducer (e.g., adapted for rotation) or an array of transducers (e.g., circumferentially positioned around the catheter) is within the spirit and scope of the present invention.

Referring back to FIG. 1, the IVUS data-acquisition system further includes a transfer-function application 114 that is adapted to use the backscattered data and an algorithm to estimate the transfer function of the catheter 120. To better understand this feature, the transfer function's relationship to the backscattered data will now be discussed.

The transfer function's influence on the backscattered data can be represented, for example, by the frequency domain equation $Z(\omega)=X(\omega)H(\omega)+E(\omega)$, where Z is the backscattered data, X is the "pure" tissue component of the backscattered data (i.e., response data for vascular tissue), H is the catheter component of the backscattered data (i.e., the transfer function), and E is the noise (or error) component of the backscattered data. Thus, once the noise component (E) is filtered out and the transfer function (H) is estimated, the response data for vascular tissue (X) can be determined by dividing the backscattered data (Z) by the transfer function (H) (i.e., $X=Z/H$).

In a preferred embodiment of the present invention, the transfer function is estimated using (i) backscattered data and (ii) an algorithm. It should be appreciated, however, that the present invention is not limited to any particular algorithm. Thus, any algorithm that uses backscattered data to estimate the transfer function of a catheter is within the spirit and scope of the present invention.

In one embodiment of the present invention, however, the algorithm is iterative and time-invariant over small intervals. For example, the frequency domain equation: $Z(\omega)=X(\omega)H(\omega)+E(\omega)$ can be rewritten in the time domain, yielding the following equation:

$$z[n] = \sum_k x[n-k]*h[k] + e[n]$$

Figure 2B:
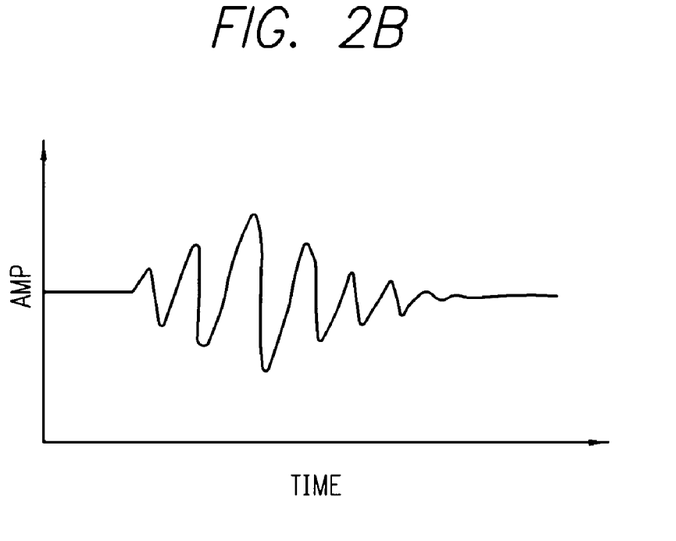
FIG. 2B illustrates exemplary ultrasound data transmitted from a transducer portion of a catheter.
Figure 2C:
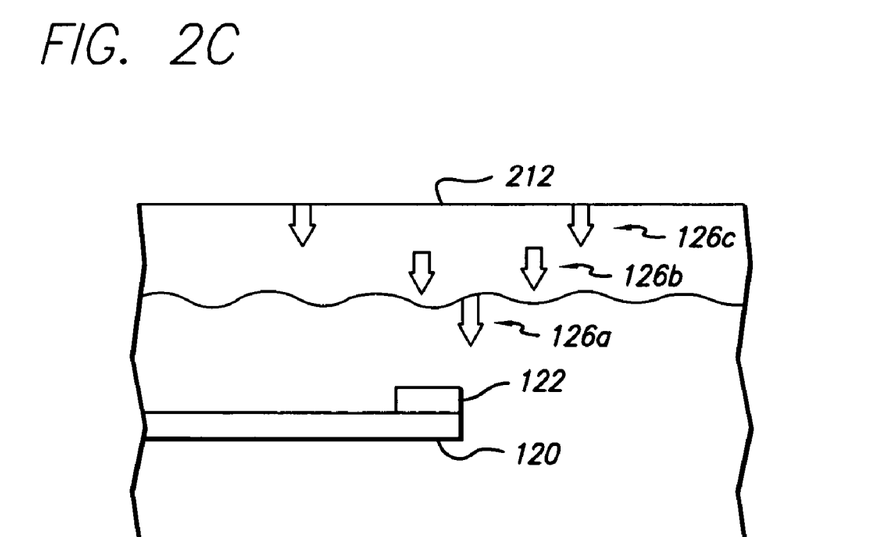
FIG. 2C illustrates exemplary ultrasound data backscattered from vascular tissue.
Figure 2D:
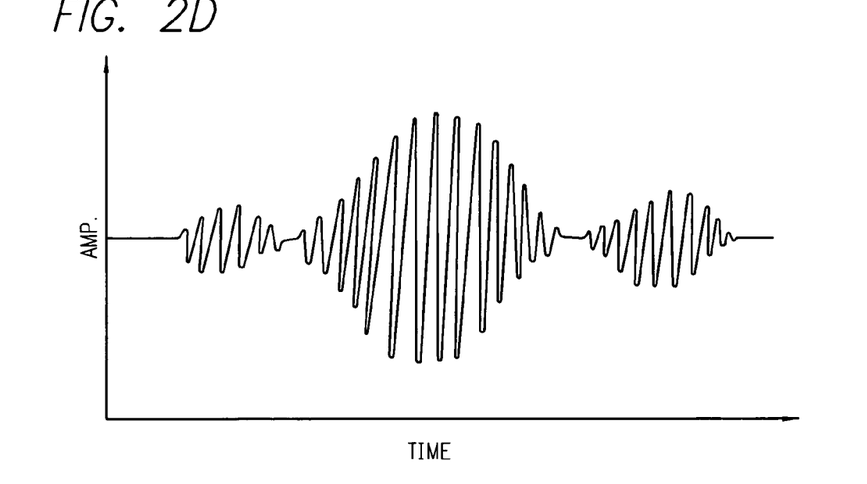
FIG. 2D illustrates exemplary ultrasound data (e.g., as backscattered from vascular tissue) received by a transducer portion of a catheter.

The backscattered ultrasound data, however, is generally backscattered at varying times (i.e., time-variant). This concept is illustrated in FIGS. 2A-2D. Specifically, FIG. 2A illustrates the use of a catheter 120 to transmit an ultrasound signal (or pulse) 124 toward vascular tissue. An exemplary ultrasound signal (e.g., like the one transmitted in FIG. 2A) is illustrated in FIG. 2B. FIG. 2C illustrates that the backscattered data is time-variant. This is because different types and densities of tissue absorb and reflect ultrasound data differently. For example, a first portion of backscattered data 126a might be represent an inner portion of vascular tissue, a second portion of backscattered data 126b might be represent a middle portion of vascular tissue, and a third portion of backscattered data 126c might be represent an outer portion of the vascular tissue. An exemplary pulse of backscattered data (e.g., like the one backscattered in FIG. 2C) is illustrated in FIG. 2D.

Thus, if the time domain equation (depicted above) is then modified using a recursive algorithm via an iterative window maximization method (i.e., to produce a time-variant equation), the aforementioned equation can be rewritten as follows:

$$z[n] = \sum_{k=0}^{K} x[n-k]h[k,n-k] + e[n]$$

If it is then assumed that the noise component is zero mean, Gaussian, white noise and the transfer function is time-invariant over small intervals, the equation becomes:

$$Z = \sum_{i=1}^{I} XiHi + e$$

Through the use of this equation, an estimate of H can be determined. One method of estimating H is to search for an estimation of X that minimizes certain error criteria (e.g., the difference between observed data and a fitted model, etc.). Once X is estimated ($X_{est}$), a least-squares-fit algorithm can be used to estimate H. In another embodiment of the present invention, the algorithm further considers certain parameters that are either selected and/or pre-specified. For example, a "scale" parameter could be pre-specified to be energy units, a "shift" parameter could be selected from the backscattered data by estimating the position of the largest sample thereof, a "sign" parameter could be selected from the backscattered data by estimating the sign of the largest sample thereof, etc.

It should be appreciated that while FIG. 1 depicts the transfer-function application 114 being executed within the computing device 110, the present invention is not so limited. Thus, for example, storing and/or executing at least a portion of the transfer-function application within another device (not shown in FIG. 1) is within the spirit and scope of the present invention. It should further be appreciated that while the transfer-function application is used to estimate the transfer function, it may also be used to perform other functions (e.g., filtering out noise (E), etc.).

In one embodiment of the present invention, the transfer function is estimated more than once during the acquisition of intravascular-ultrasound (IVUS) data. Specifically, the acquisition of IVUS data typically includes (i) maneuvering a catheter through a vascular structure (e.g., a blood vessel) of a patient and (ii) acquiring IVUS data while the catheter is being moved through the structure (e.g., pulled back through the structure). However, because the transfer function may change over time (e.g., due to the degradation of components associated thereto, etc.), it may be advantageous to estimate (or re-estimate) the transfer function at different times and/or locations. For similar reasons, in another embodiment of the present invention, the transfer function is estimated continuously (or substantially continuously) for at least a portion of the time that the catheter is within a particular vascular structure.

In a preferred embodiment of the present invention, the transfer function (H) and the backscattered data (Z) are used to calculate the response data (X) (e.g., X=Z/H). In another embodiment of the present invention, the transfer function (H), the backscattered data (Z), and the estimated response data ($X_{est}$) are used to calculate the response data (X). For example, the transfer function (H) and the backscattered data (Z) could be used to calculate the response data ($X_{cal}$) (e.g., $X_{cal}$=Z/H) and the calculated response data ($X_{cal}$) and the estimated response data ($X_{est}$) could be used to calculate the response data for vascular tissue (X) (e.g., X is a function of $X_{cal}$ and $X_{est}$). In another embodiment of the present invention, the estimated response data ($X_{est}$), alone (i.e., without the calculated response data ($X_{cal}$)), is used to calculate the response data (X) (e.g., $X_{est}$=X, etc.).

Figure 3:
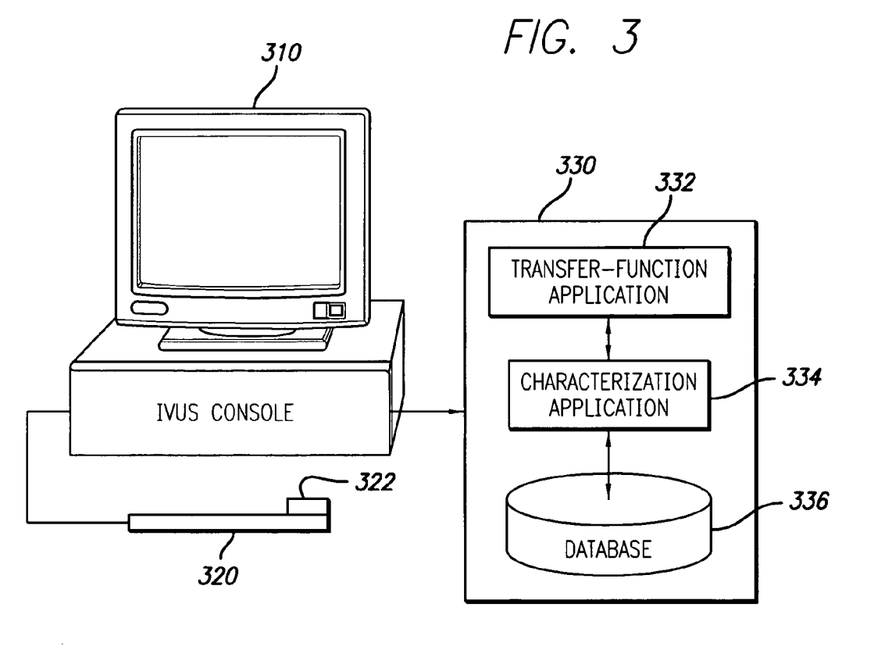
FIG. 3 illustrates a vascular-tissue-characterization system in accordance with one embodiment of the present invention, including an intravascular-ultrasound (IVUS) console, a catheter having a transducer, and a computing device.

FIG. 3 illustrates a vascular-tissue-characterization system operating in accordance with a second embodiment of the present invention. In this embodiment, an IVUS console 310 is electrically connected to a catheter 320 and a computing device 330, wherein the computing device 330 includes at least a transfer-function application 332, a characterization application 334, and a database 336. The IVUS console 310 is used to acquire RF backscattered data from a vascular structure. Specifically, a transducer 322 is attached to the end of the catheter 320 and used (as previously discussed) to acquire ultrasound data backscattered from vascular tissue. The backscattered data is then transmitted to the computing device 330 via the IVUS console 310. Once the backscattered data is received, the transfer-function application 332 is used (as previously discussed) to estimate the transfer function (H) and to calculate the response data (X). The response data (X) and histology data (e.g., as stored in the database 336) are then used by the characterization application 334 to characterize at least a portion of the vascular tissue (e.g., identifying tissue type, etc.).

It should be appreciated that the IVUS console 310 depicted herein is not limited to any particular type of IVUS console, and includes all ultrasound devices generally known to those skilled in the art (e.g., Boston Scientific Clearview Imaging System, etc.). It should also be appreciated that the database 336 depicted herein includes, but is not limited to, RAM, cache memory, flash memory, magnetic disks, optical disks, removable disks, SCSI disks, IDE hard drives, tape drives and all other types of data storage devices (and combinations thereof, such as RAID devices) generally known to those skilled in the art. It should further be appreciated that the transfer-function application 332 and the characterization application 334 may exist as a single application or as multiple applications (i.e., more than one), locally and/or remotely stored.

Referring back to FIG. 3, the characterization application 334 is adapted to receive response data (X), to determine parameters related thereto, and use parameters stored in the database 336 (i.e., histology data) to identify tissue type(s) or characterization(s) thereof. Specifically, prior to the acquisition of the response data (e.g., from the transfer-function application 332), parameters are stored in the database 336 and linked to characterization data. Once the response data is acquired, the characterization application 334 is used to identify at least one parameter associated (either directly or indirectly) with the response data. The identified parameters are then compared to the parameters stored in the database (i.e., histology data). If a match (either exactly or substantially) is found, the related region (i.e., at least a portion of the vascular tissue) is correlated to the tissue type stored in the database 336 (e.g., as linked to the matching parameter(s)).

It should be appreciated that each parameter stored in the database 336 may be associated with more than one tissue type or characterizations. For example, a first parameter may be common to multiple tissue types, thus requiring additional parameters to narrow the field. It should also be appreciated that a match may occur as long as the parameters fall within a range of properties for a particular tissue type found in the database 336. It should further be appreciated that the terms "tissue type" and "characterization," as these terms are used herein, include, but are not limited to, fibrous tissues, fibro-lipidic tissues, calcified necrotic tissues, calcific tissues, collagen, cholesterol, thrombus, compositional structures (e.g., the lumen, the vessel wall, the medial-adventitial boundary, etc.) and all other identifiable characteristics generally known to those skilled in the art.

In one embodiment of the present invention, the characterization application 334 is adapted to identify parameters directly from the response data (X), which is in the time domain. In another embodiment of the present invention, the characterization application 334 is adapted to perform signal analysis (i.e., frequency analysis, etc.) on the response data (X) before the parameters are identified. In other words, for example, the response data (X) might be converted (or transformed) into the frequency domain before parameters are identified. In another embodiment of the present invention, the characterization application 334 is adapted to identify parameters from both the response data (X) and its frequency spectrum. This is because the response data, which is in the time domain, can be used to spatially identify certain frequencies (or parameters related thereto). For example, if a vascular structure comprises multiple tissue layers, corresponding backscattered data can be used to identify the location of these tissues and the related frequency spectrum can be used to identify tissue types (see e.g., FIGS. 2C and 2D). These concepts are discussed in more detail in U.S. Pat. No. 6,200,268 and patent application Ser. No. 10/647,971 (as previously identified)

It should be appreciated that, while certain embodiments have been described in terms of frequency transformation, the present invention is not so limited. Thus, alternate transformations (e.g., wavelet transformation, etc.) are within the spirit and scope of the present invention. It should also be appreciated that the term parameter, as that term is used herein, includes, but is not limited to maximum power, minimum power, frequencies at maximum and/or minimum power, y intercepts (estimated or actual), slope, mid-band fit, integrated backscatter and all parameters generally known to (or discernable by) those skilled in the art. It should be further appreciated that the response data may either be received and/or analyzed (e.g., to identify parameters) in real-time (e.g., while the catheter is in the patient) or after a period of delay.

In one embodiment of the present invention, the characterization application 334 is further adapted to display a reconstructed image of at least a portion of the interrogated vascular structure on a display (e.g., the IVUS console 310, a computing device display (not shown), etc.). In the image, each tissue type (or characterization) is distinguished by using gray-scales or colors (e.g., different colors correspond to different tissue types, etc.). Such a system makes different tissue types or characterizations easily identifiable.

Figure 4:
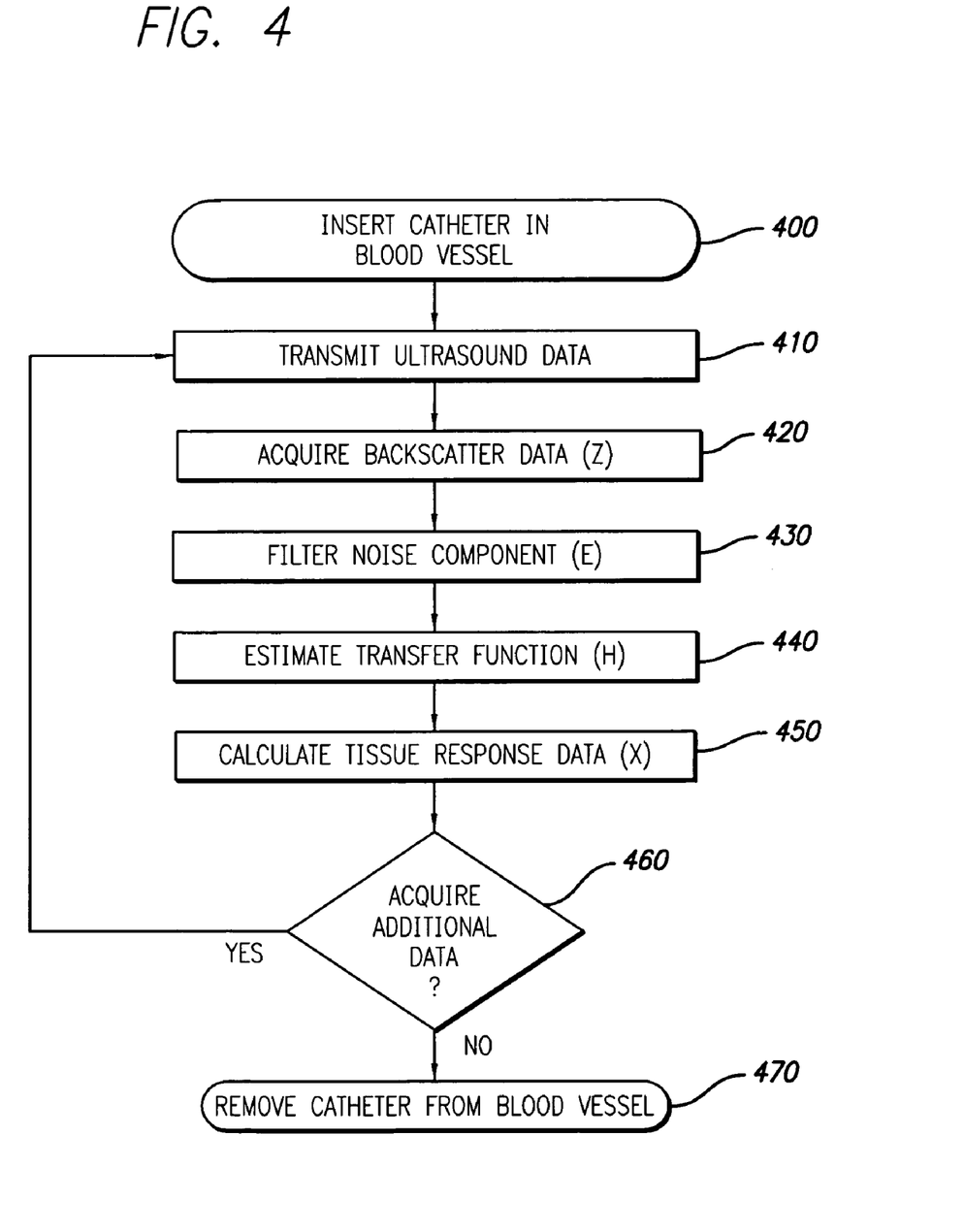
FIG. 4 illustrates a method of calculating ultrasound response data for vascular tissue.

One method of acquiring response data for vascular tissue is illustrated in FIG. 4. Specifically, at step 400, a catheter having at least one transducer is inserted into a vascular structure (e.g., blood vessel). The catheter is then used to transmit ultrasound data toward a tissue portion of the vascular structure (i.e., vascular tissue) at step 410. Ultrasound data backscattered from the vascular tissue (Z) is then acquired at step 420. At step 430, a noise component (E) of the backscattered ultrasound data (Z) is filtered (e.g., removed, reduced, etc.). At step 440, the backscattered ultrasound data (Z) is used to estimate the catheter's transfer function (H). In one embodiment of the present invention, this step is performed in real-time (e.g., while multiple sets of backscattered data are being acquired, while the catheter is in the vascular structure, etc.). At step 450, the estimated transfer function (H) is used to calculate response data for the vascular tissue (X). If additional data is to be acquired (i.e., step 460), then the process repeats (i.e., starting at step 410). If no more data is needed, then the catheter is removed from the vascular structure at step 470. It should be appreciated that the order in which these steps are presented is not intended to limit the present invention. Thus, for example, filtering the noise component (E) after the transfer function (H) is estimated is within the spirit and scope of the present invention.

Having thus described embodiments of a system and method of using ultrasound data backscattered from vascular tissue to estimate the transfer function of a catheter, it should be apparent to those skilled in the art that certain advantages of the system have been achieved. It should also be appreciated that various modifications, adaptations, and alternative embodiments thereof may be made within the scope and spirit of the present invention. The invention is further defined by the following claims.

What is claimed is:

1. A method of acquiring ultrasound response data for vascular tissue, comprising:

maneuvering at least a portion of a catheter through a vascular structure to a first location for acquiring ultrasound echoes from a first portion of vascular tissue;

transmitting an ultrasound signal toward the first portion of vascular tissue and acquiring first backscattered ultrasound data therefrom;

using at least a portion of said first backscattered ultrasound data and an algorithm incorporating an estimate of a tissue component of backscattered ultrasound data to estimate a first transfer function of said catheter;

calculating first ultrasound response data using at least said first transfer function, said first ultrasound response data being (i) indicative of data that is backscattered from vascular tissue and (ii) substantially independent from ultrasound data modifications resulting from said catheter;

repositioning the at least a portion of the catheter through the vascular structure to a second location for acquiring ultrasound echoes from a second portion of vascular tissue;

transmitting an ultrasound signal toward the second portion of vascular tissue and acquiring second backscattered ultrasound data therefrom;

using at least a portion of said second backscattered ultrasound data and an algorithm incorporating an estimate of a tissue component of backscattered ultrasound data to estimate a second transfer function of said catheter; and calculating second ultrasound response data using at least said second transfer function, said second ultrasound response data being (i) indicative of data that is backscattered from vascular tissue and (ii) substantially independent from ultrasound data modifications resulting from said catheter.

2. The method of claim 1, further comprising the step of filtering noise from said first backscattered ultrasound data.

3. The method of claim 1, wherein said algorithm is an iterative algorithm that is time-invariant over small intervals.

4. The method of claim 1, wherein said step of using at least a portion of said first backscatter ultrasound data and said algorithm to estimate the first transfer function of said catheter comprises the step of using an error-criteria algorithm and a least-squares-fit algorithm to estimate ultrasound response data for said vascular tissue and said first transfer function of said catheter, respectively.

5. The method of claim 4, further comprising the step of using said estimated ultrasound response data and said calculated first ultrasound response data to calculate final ultrasound response data for said vascular tissue.

6. The method of claim 1, further comprising the step of using at least said first ultrasound response data to produce an ultrasound image of vascular tissue.

7. The method of claim 1, further comprising the steps of:
identifying a plurality of parameters of said first ultrasound response data; and
using said plurality of parameters and previously stored histology data to characterize at least a portion of said vascular tissue.

8. The method of claim 7, further comprising the steps of:
transforming said first ultrasound response data from a time domain into a frequency domain; and
identifying at least two of said plurality of parameters from the frequency spectrum of said first ultrasound response data.

9. The method of claim 8, wherein said step of identifying said at least two of said plurality of parameters further comprises selecting said at least two parameters from the group consisting of: maximum power, minimum power, frequency at maximum power, frequency at minimum power, y intercept, slope, mid-band fit, and integrated backscatter.

10. The method of claim 7, wherein said step of using said plurality of parameters and previously stored histology data to characterize at least a portion of said vascular tissue further comprises using said plurality of parameters and said previously stored histology data to identify a tissue type of at least a portion of said vascular tissue, said tissue type being selected from the group consisting of: fibrous tissues, fibrolipidic tissues, calcified necrotic tissues, and calcific tissues.

11. The method of claim 10, further comprising the step of using at least said identified tissue type to produce a tissue-characterization image of at least said portion of said vascular tissue on a display.

* * * * *